United States Patent
Lee et al.

(10) Patent No.: US 11,557,379 B2
(45) Date of Patent: Jan. 17, 2023

(54) APPARATUS AND METHOD FOR PREDICTING DISPERSION OF HAZARDOUS AND NOXIOUS SUBSTANCES

(71) Applicant: Korea Institute of Ocean Science & Technology, Daejeon (KR)

(72) Inventors: Moon Jin Lee, Daejeon (KR); Sang Woo Oh, Sejong (KR); Ho-Jin Hwang, Dajeon (KR)

(73) Assignee: Korea Institute of Ocean Science & Technology, Daejeon (KR)

( * ) Notice: Subject to any disclaimer, the term of this patent is extended or adjusted under 35 U.S.C. 154(b) by 1284 days.

(21) Appl. No.: 15/775,929

(22) PCT Filed: Oct. 5, 2016

(86) PCT No.: PCT/KR2016/011124
§ 371 (c)(1),
(2) Date: May 14, 2018

(87) PCT Pub. No.: WO2017/086595
PCT Pub. Date: May 26, 2017

(65) Prior Publication Data
US 2018/0330064 A1 Nov. 15, 2018

(30) Foreign Application Priority Data
Nov. 17, 2015 (KR) ........................ 10-2015-0161214

(51) Int. Cl.
*G01W 1/00* (2006.01)
*G01C 13/00* (2006.01)
(Continued)

(52) U.S. Cl.
CPC ............. *G16C 20/70* (2019.02); *G01C 13/00* (2013.01); *G01P 13/02* (2013.01); *G01W 1/00* (2013.01);
(Continued)

(58) Field of Classification Search
CPC .... G01C 13/006; G01C 13/004; G01C 13/00; G01C 13/002; G01C 13/008; G01C 5/06;
(Continued)

(56) References Cited

FOREIGN PATENT DOCUMENTS

| CN | 102156817 A | 8/2011 | |
|---|---|---|---|
| CN | 107944608 A * | 4/2018 | ............. G06F 16/29 |

(Continued)

OTHER PUBLICATIONS

"Response Techniques for Chemical Contamination Accident at sea". Oil Spill Technical Information Papers, National Maritime Police Agency, Jun. 30, 2014.
(Continued)

*Primary Examiner* — Andre J Allen
(74) *Attorney, Agent, or Firm* — Harness, Dickey & Pierce, P.L.C.

(57) ABSTRACT

The present invention relates to an apparatus and a method for predicting the dispersion of hazardous and noxious substances and, more specifically, provides an apparatus and a method for predicting the dispersion of hazardous and noxious substances, the method: checking the components of the hazardous and noxious substances having leaked into the ocean, so as to classify the hazardous and noxious substances into a corresponding classification set among twelve classification sets by means of at least one of vapor pressure, the degradation in water, or density; dividing the classification sets, in which the hazardous and noxious substances are classified, into one dispersion model among an air dispersion model, a seawater dispersion model, and an air/seawater dispersion model according to the dispersion characteristics thereof; acquiring, from a weather center server, the state information of a sea area, which is set to be different according to the divided dispersion models; and predicting a danger radius for the dispersion of the hazard-
(Continued)

ous and noxious substances by using the acquired state information of the sea area, and outputting the same.

9 Claims, 3 Drawing Sheets

(51) Int. Cl.
*G01P 13/02* (2006.01)
*G01P 5/00* (2006.01)
*G06Q 50/26* (2012.01)
*G16C 20/70* (2019.01)
*G16C 20/30* (2019.01)

(52) U.S. Cl.
CPC ............ *G06Q 50/26* (2013.01); *G16C 20/30* (2019.02); *G01P 5/00* (2013.01)

(58) Field of Classification Search
CPC ........ G01C 17/34; G01C 21/16; G01C 25/00; G01C 5/04; G01C 9/00; G01C 9/06; G01C 9/14; G01C 9/18; G01C 9/12; G01P 13/02; G01P 5/00
USPC .......................................... 73/170.29–170.34
See application file for complete search history.

(56) References Cited

FOREIGN PATENT DOCUMENTS

| | | | | | |
|---|---|---|---|---|---|
| CN | 112016226 | B | * | 5/2021 | ............ G06F 30/23 |
| CN | 110399676 | B | * | 12/2021 | |
| JP | 2006-131126 | A | | 5/2006 | |
| KR | 10-0799602 | B1 | | 2/2008 | |
| KR | 10-1489891 | B1 | | 2/2015 | |
| KR | 10-1567431 | B1 | | 11/2015 | |
| KR | 101963320 | B1 | * | 7/2017 | |
| KR | 101868791 | B1 | * | 12/2017 | |

OTHER PUBLICATIONS

International Search Report PCT/ISA/210 for International Application No. PCT/KR2016/01112 dated Dec. 19, 2016.

* cited by examiner

[Figure 1]
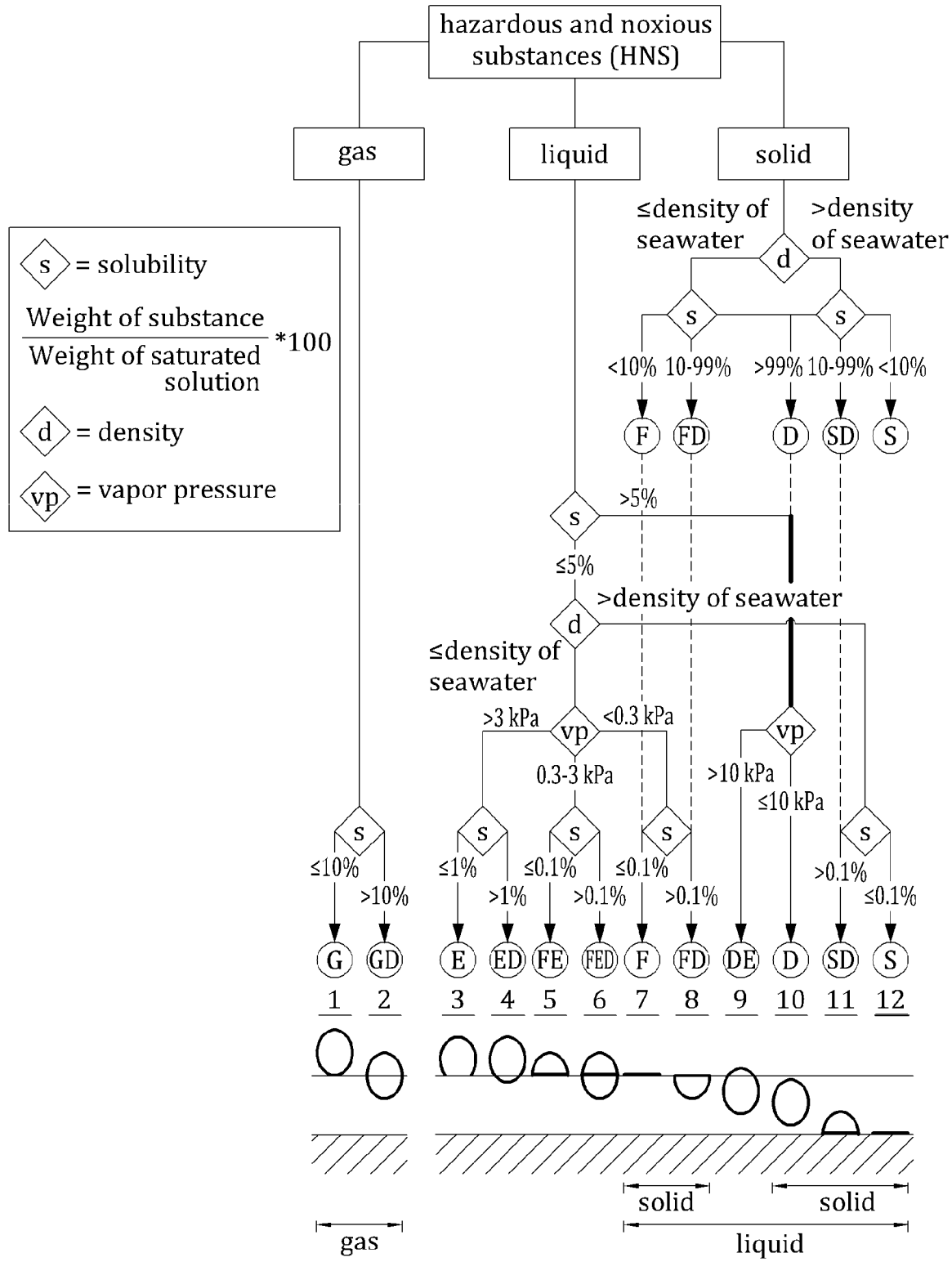

[Figure 2]
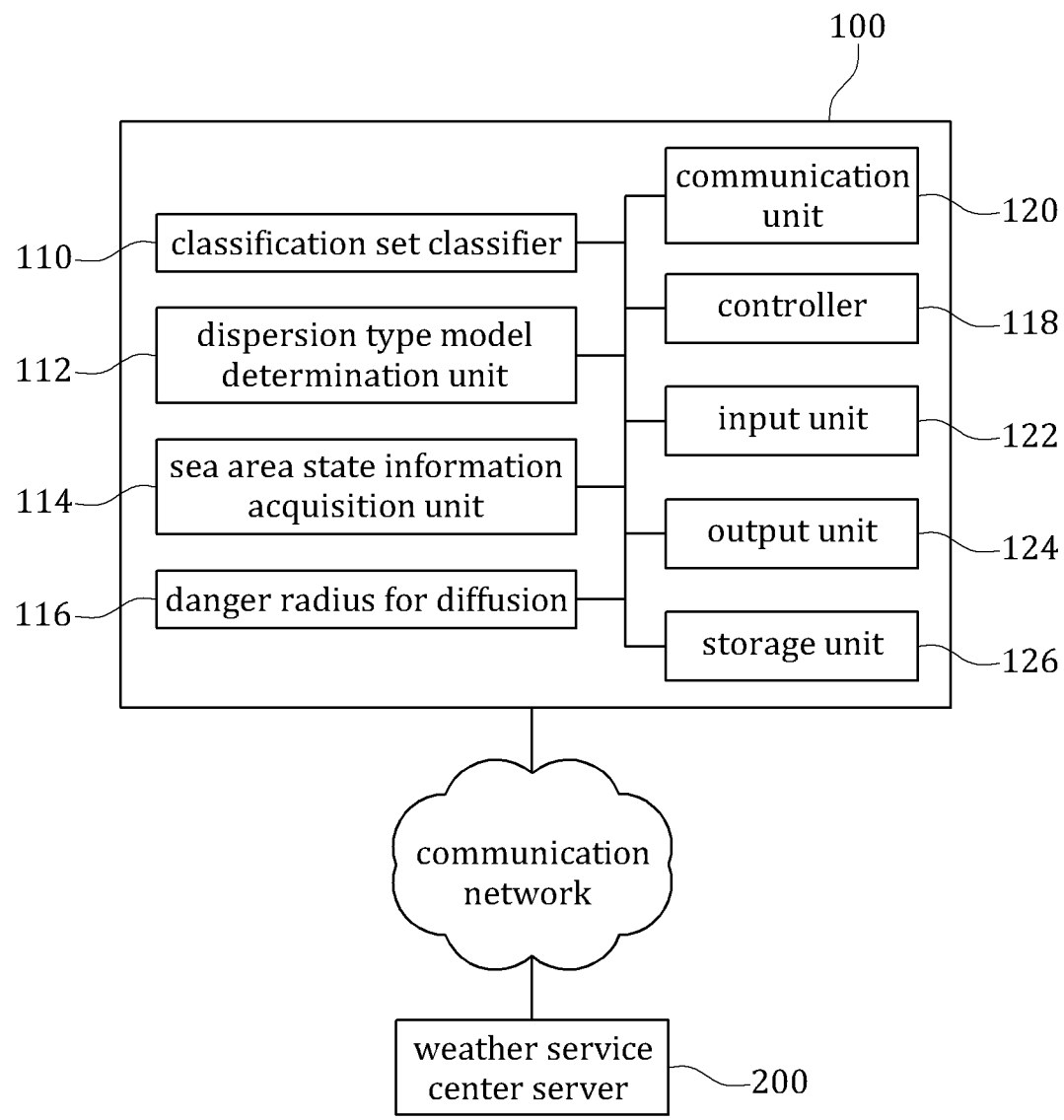

[Figure 3]
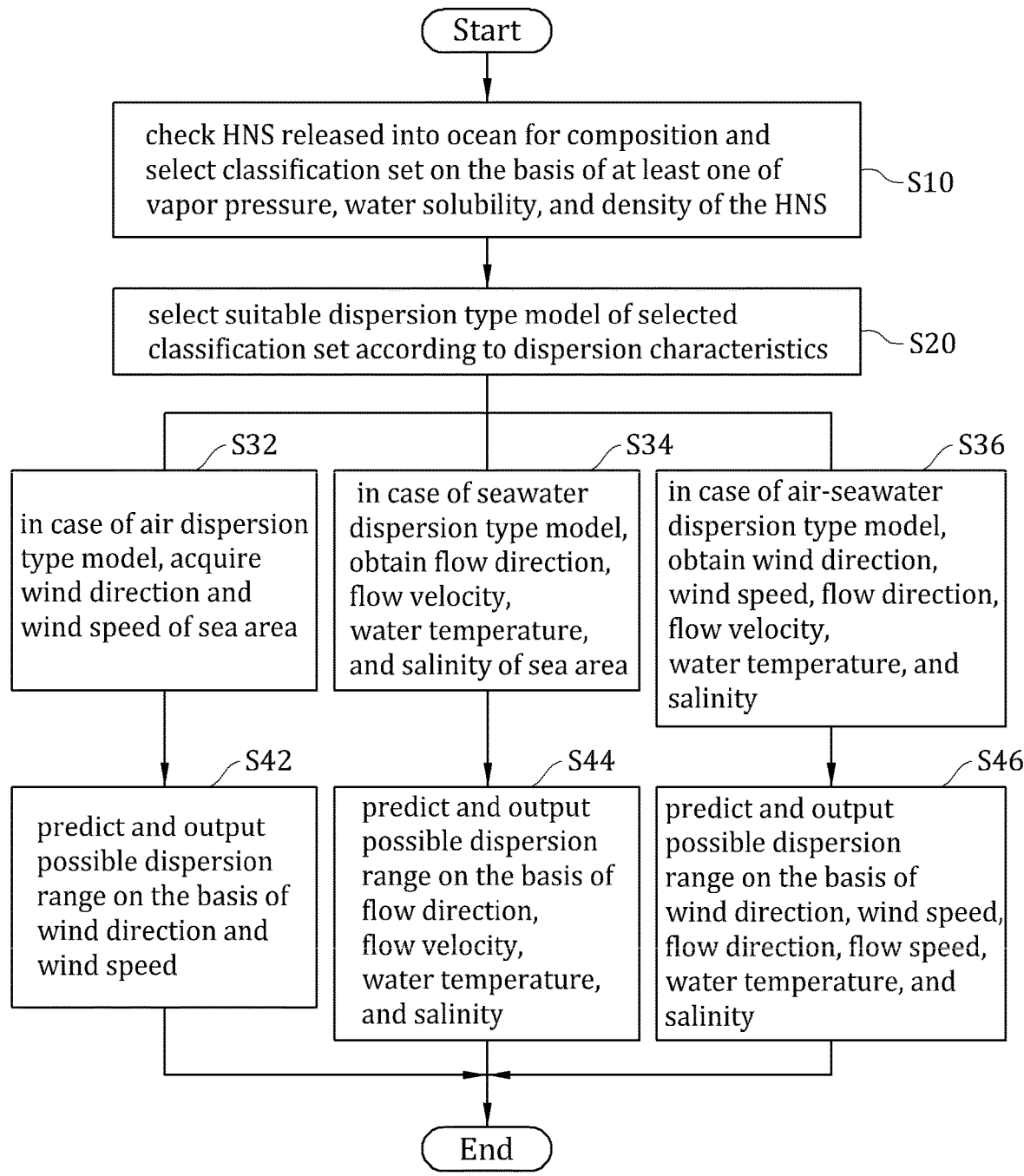

APPARATUS AND METHOD FOR PREDICTING DISPERSION OF HAZARDOUS AND NOXIOUS SUBSTANCES

CROSS-REFERENCE TO RELATED APPLICATIONS

This application is a national phase under 35 U.S.C. § 371 of PCT International Application No. PCT/KR2016/011124 which has an International filing date of May 10, 2016, which claims priority to Korean Application No. 10-2015-0161214, filed Nov. 17, 2015, the entire contents of each of which are hereby incorporated by reference.

TECHNICAL FIELD

The present invention relates to an apparatus for and a method of predicting the dispersion radius of hazardous and noxious substances (HNS). More particularly, the present invention relates to an HNS dispersion prediction apparatus and method of performing the following steps: identifying a composition of a hazardous and noxious substance (HNS) released in the event of a marine spill accident; selecting one classification set to which the NHS belongs from among 12 HNS classification sets, on the basis of at least one parameter among vapor pressure, water solubility, and density; determining a suitable dispersion model for the classification set of the released HNS, from among an air dispersion model, a seawater dispersion model, and an air-seawater dispersion model, according to the dispersion characteristics of the released HNS; acquiring state information of a sea area which is around the location of the marine spill accident and which is differently set according to the determined suitable dispersion model, from a weather service center server; predicting a danger radius for HNS dispersion by using the selected dispersion model and the obtained state information; and outputting the danger radius, whereby the apparatus and method allows a quick and efficient response to the marine spill accident by providing information of the danger radius for HNS diffusion.

BACKGROUND ART

Recently, international transportation of HNS, which mostly relies on maritime transportation, is increasing rapidly. Also, due to recent emphasis on the economies of scale and the development of technology, the maritime transportation environment is changing. For example, the maritime transport market is currently witnessing a trend for preference for larger and faster ships. As a result, hazardous and noxious substances (HNS), such as crude oil, refined petroleum products, and chemical substances, can be transported in bulk to maximize efficiency, but the spillage risk is also increasing due to the increase in the total volume of transport.

Therefore, interest in safety management especially for hazardous and noxious substances (HNS) is increasing due to the increase of the hazardous and noxious substance traffic volume and the recognition of the risk of domestic and international pollution accidents.

In particular, the hazardous and noxious substances transported by sea are very diverse, with more than 6,000 species, and the type and nature of the accidents that may occur due to their release are complex, so that development of technologies for predicting and monitoring a dispersion state of HNS is required.

However, existing countermeasures against marine spill accidents have been limited to technologies for dealing with oil pollution. Therefore, additional countermeasures against various kinds of hazardous and noxious substances are required to cope with marine spill accidents of those substances. In particular, in case of marine spills of hazardous and noxious substances, a technology for rapidly and accurately predicting a danger radius for dispersion is required.

DISCLOSURE OF THE INVENTION

Technical Problem

The present invention has been made in order to solve the problems occurring in the related art, and an objective of the present invention is to an HNS dispersion prediction apparatus and method being capable of rapidly and easily predicting a danger radius for dispersion of a released hazardous and noxious substance to rapidly and effectively respond to a marine spill accident, the apparatus and method performing the following steps for this purpose: identifying a composition of a hazardous and noxious substance which may be released in the event of a marine spill accident; selecting one classification set to which the released hazardous and noxious substance belongs, from among 12 classification sets, on the basis at least one parameter of vapor pressure, solubility, and density; determining a suitable dispersion model for the hazardous and noxious material among an air dispersion model, a seawater dispersion module, and an air-seawater dispersion model, depending on the dispersion characteristics of the released hazardous and noxious substance; acquiring state information of a sea area which is located around a marine spill accident region and is differently set according to the determined dispersion model, from a server of a weather service center; predicting a danger radius for dispersion by using the selected dispersion model and the state information of the sea area; and providing information on the danger radius for dispersion.

Technical Solution

In order to accomplish the above objective, an HNS dispersion prediction apparatus according to one embodiment of the present invention includes: a classification set classifier for determining a classification set to which a hazardous and noxious substance revealed by a marine spill accident belongs, from among 12 classification sets that are classified sets of hazardous and noxious substances, on the basis of at least one parameter selected from among vapor pressure, solubility, and density of each substance; a dispersion model determination unit for determining a suitable dispersion model for the selected classification set according to dispersion characteristics of the released hazardous and noxious substance, from among an air dispersion model, a seawater dispersion module, and an air-seawater dispersion model; a sea area state information acquisition unit for acquiring state information of a sea area which is differently set according to the determined dispersion model, from an external server; a danger radius prediction unit for predicting a danger radius for dispersion by using the acquired stage information of the sea area; and a controller for controlling the classification set classifier, the dispersion model determination unit, the sea area state information acquisition unit, and the danger radius prediction unit, thereby controlling overall operation required for predicting the danger radius for dispersion.

In order to accomplish the above objectives, an HNS dispersion prediction method according to another embodiment of the present invention includes: identifying a composition of a hazardous and noxious substance released into the ocean; determining a classification set to which the hazardous and noxious substance belongs, on the basis of at least one parameter of vapor pressure, solubility, and density, from among 12 classification sets; determining which dispersion model among an air dispersion model, a seawater dispersion module, and an air-seawater dispersion module is suitable for the classification set to which the released HNS belongs, according to dispersion characteristics of the determined classification set; acquiring state information of a sea area which is around an HNS release area and which is differently set according to the determined dispersion model; predicting a danger radius for dispersion of the HNS by using the acquired state information of the sea area; and outputting the danger radius.

Advantageous Effects

According to the present invention, when there is a maritime spill accident of hazardous and noxious substances (HNSs), the following steps are performed: identifying a composition of the HNS; determining a classification set to which the HNS belongs on the basis of at least one parameter of vapor pressure, solubility, and density, from among 12 classification sets of HNSs; determining which dispersion model among an air dispersion model, a seawater dispersion module, and an air-seawater dispersion model is suitable as a dispersion model of the released HNS, on the basis of dispersion characteristics of the classification set of the HNS; acquiring state information of a sea area which is located around a maritime spill accident region and is differently set according to the determined dispersion model; predicting a danger radius for dispersion of the HNS; and outputting the danger radius, whereby the present invention has an advantage of rapidly and easily predicting a danger radius, thereby enabling rapid and efficient countermeasures against the released hazardous and noxious substance.

Considering the speed and efficiency of prediction of a danger radius for dispersion, according to the present invention, hazardous and noxious substances (HNSs) are classified into a gas phase type, a liquid phase type, and a solid phase type. Then, the HNSs are further classified into several classification sets on the basis of at least one parameter among vapor pressure, water solubility, and density. Then, a suitable dispersion model for the classification set to which a corresponding HNS belongs is selected from among an air dispersion type, a seawater dispersion type, and an air-seawater dispersion type, according to the dispersion characteristics of the corresponding classification set, instead of considering the characteristics of all the hazardous and noxious substances of all kinds that are insignificantly different from each other. Furthermore, the present invention uses different types of state information of a sea area which is located around a spill accident region and is differently set according to the selected dispersion model, to predict a danger radius for dispersion. Therefore, the present invention has an advantage of producing a quick and reliable prediction result.

BRIEF DESCRIPTION OF THE DRAWINGS

FIG. 1 is a diagram illustrating an exemplary classification method for hazardous and noxious substances;

FIG. 2 is a block diagram illustrating a dispersion prediction apparatus for hazardous and noxious substances, according to one embodiment of the present invention; and FIG. 3 is a flowchart illustrating a dispersion prediction method for hazardous and noxious substances, according to another embodiment of the present invention.

MODE FOR CARRYING OUT THE INVENTION

Hereinafter, preferred embodiments of the present invention will be described below with reference to the accompanying drawings. In describing the embodiments of the present invention, well-known functions or constructions will not be described in detail when it is determined that they may obscure the spirit of the present invention.

Embodiments according to the idea or concept of the present invention may be modified in various different ways and may have various different forms. Therefore, only particular embodiments may be illustrated in the drawings and will be described in detail herein. Meanwhile, the embodiments described in the specification and the configurations illustrated in the drawings are merely examples and do not exhaustively present the technical spirit of the present invention. Therefore, it should be noted that the present invention is not limited to the embodiments according to the concept of the present invention but may cover all modifications, equivalents, and substitutes thereof.

It is to be understood in the following description that when one component is referred to as being "connected to", or "coupled to" another component, it may include not only direct connection, but indirect connection with another component therebetween. However, when one component is referred to as being "directly connected to" or "directly coupled to" another component, there is no intervening component therebetween. Other expressions regarding relationships between components, such as "therebetween", "directly between", "adjacent to", and "directly adjacent to" should be construed likewise.

The terminology used herein is for the purpose of describing particular embodiments only and is not intended to be limiting of the invention. The singular forms "a," "an," and "the" include plural referents unless the context clearly dictates otherwise. It will be further understood that the terms "comprise", "include", "have", etc. when used in the present disclosure specify the presence of stated features, integers, steps, operations, elements, components, and/or combinations thereof but do not preclude the presence or addition of one or more other features, integers, steps, operations, elements, components, and/or combinations thereof.

Hereinafter, a dispersion prediction apparatus and method for hazardous and noxious substances, according to preferred embodiments of the present invention, will be described in detail with reference to the accompanying drawings.

FIG. 1 is a diagram illustrating an exemplary method of classifying hazardous and noxious substances, which is used in the present invention.

More than 6,000 hazardous and noxious substances can be classified into a gas phase, a liquid phase, and a solid phase. In addition, various kinds of hazardous and noxious substances can be further classified into 12 classification sets according to one or more parameters among water solubility, density, and vapor pressure.

The 12 classification sets consist of a gas (G) classification set, a dissolver/gas (GD) classification set, an evaporator (E) classification set, an evaporator/dissolver (ED) classification set, a floater/evaporator (FD) classification set, a dissolver/evaporator (DE) classification set, a dissolver (D) classification set, a sinker/dissolver (SD) classification set, a floater (SD) classification set, and a sinker (S) classification set.

For example, as shown in FIG. 1, when a hazardous and noxious substance which is a gas phase substance has a solubility s of 10% or lower, it may be classified as a gas (G) classification set among 12 classification sets. Hazardous and noxious substances classified as the gas (G) classification set 1 have the characteristic of diffusing into the air A of a sea area around a marine spill accident region. Therefore, the gas (G) classification set 1 is considered to disperse according to an air dispersion model.

Also, when a certain hazardous and noxious substance that is a solid phase substance has a density d higher than that of seawater and a solubility s of 10% to 99%, it is classified as a sinker/dissolver (SD) classification set 11. Hazardous and noxious substances classified as the sinker/dissolver (SD) classification set 11 have characteristics of dissolving and sinking in seawater, thereby dispersing into seawater B and to the bottom C of the sea around the marine spill accident region. Therefore, the sinker/dissolver (SD) classification set 11 is considered to disperse according to an air-seawater dispersion model.

Thus, a suitable dispersion model for each of the twelve classification sets is determined as being the air dispersion model, the seawater dispersion model, or the air-seawater dispersion model, depending on the dispersion characteristics thereof. A suitable dispersion model for the gas (G) classification set and the evaporator (E) classification set may be the air dispersion model. A suitable dispersion model for the floater (F) classification set, the floater/dissolver (FD) classification set, the dissolver (D) classification set, the sinker/dissolver (SD) classification set, and the sinker (S) classification set may be the seawater dispersion model. A suitable dispersion model for the evaporator/dissolver (ED) classification set, the evaporator/dissolver (ED) classification set, the floater/evaporator (FE) classification set, the floater/evaporator/dissolver classification set, and the dissolver/evaporator (DE) classification set may be the air-seawater dispersion model.

Thus, various kinds of hazardous and noxious substances are first classified into 12 classification sets by at least one parameter among vapor pressure, solubility, and density. Then, a dispersion model for each classification set is determined among the air dispersion type, the seawater dispersion type, and the air-seawater dispersion type. The classification results may be stored in a memory device of a computer. Thus, the present invention allows a quick and easy determination of which hazardous and noxious substance is included in which classification set and applies to which dispersion model.

FIG. 2 is a block diagram of an apparatus for predicting dispersion of hazardous and noxious substances (HNS), which will be simply referred to as an HNS dispersion prediction apparatus hereinafter, according to one embodiment of the present invention. As illustrated in FIG. 2, an HNS dispersion prediction apparatus 100 includes: a classification set classifier 110 for classifying a hazardous and noxious substance (HNS) resulting from a marine spill accident as a corresponding classification set among 12 classifications by at least one of vapor pressure, solubility, and density of the substance; a dispersion model determination unit 112 for determining a suitable dispersion model of the classification set of the HNS by selecting one model among an air dispersion model, a seawater dispersion model, and an air-seawater dispersion model according to the dispersion characteristics of the substances of the corresponding classification set; a sea area state information acquisition unit 114 for acquiring state information of a relevant sea area that is set according to the determined dispersion model, from an external server; a danger radius prediction unit 116 for predicting a danger radius for dispersion by using the obtained state information of the sea area; and a controller 118 for controlling the classification set classifier 110, the dispersion model determination unit 112, the sea area state information acquisition unit 114, and the danger radius prediction unit 116, thereby controlling overall operation required for prediction of a danger radius for dispersion.

The HNS dispersion prediction apparatus further includes a communication unit 120 for communicating with an external device or an external server, an input unit 122, an output unit 124, and a storage unit 126.

The input unit 122 is a device with which known characteristic information (including material phase, water solubility, density, vapor pressure, etc.) of hazardous and noxious substances that may be released into the ocean can be input. The output unit 124 outputs the known characteristic information of the hazardous and noxious substances that are input through the input device, and outputs calculated danger radius for dispersion of a hazardous and noxious substance. The storage unit 126 may store the known characteristic information on hazardous and noxious substances that have been recorded thereon in advance. The storage unit 126 may also store information on the state information of the sea area, that is, information including wind direction, wind speed, flow direction of seawater, flow velocity, water temperature, salinity, etc. obtained from a weather service center server 200.

FIG. 3 is a flowchart illustrating a method of predicting dispersion of hazardous and noxious substances (HNS), which will be simply referred to as a HNS dispersion prediction method for convenience of description hereinafter, according to another embodiment of the present invention. As illustrated in FIG. 3, the HNS dispersion prediction method according to another embodiment of the present invention includes: a first step S10 of identifying a composition of a hazardous and noxious substance released into the ocean and classifying the hazardous and noxious substance as one classification set among 12 classification sets by at least one parameter among vapor pressure, water solubility, and density; a second step S20 of determining a suitable dispersion model of the determined classification set of the hazardous and noxious substance by selecting one model among an air dispersion model, a seawater dispersion model, and an air-seawater dispersion model according to dispersion characteristics; and a third step S32, S34, S36, S42, S44, S46 of acquiring state information of a sea area which is set around a marine spill accident region and which is differently set according to the determined dispersion model, from an external server, and predicting and outputting a danger radius for dispersion of the released HNS by using the obtained state information of the sea area.

The operation of the HNS dispersion prediction apparatus according to the embodiment of the present invention will be described in detail.

First, the classification set classifier 110 identifies a composition of a hazardous and noxious substance released into the ocean, and classifies the hazardous and noxious substance as one classification set of the 12 classification sets illustrated in FIG. 1 by at least one of vapor pressure, water solubility, and density (S10). The vapor pressure, water solubility, and density of hazardous and noxious substances may be stored in the storage unit 126, may be input with the input device 122, or may be externally transmitted through the communication unit 120.

The dispersion model determination unit 112 determines a suitable dispersion model for the classification set of the hazardous and noxious substance, which is determined by the classification set classifier 110, by selecting one dispersion model among an air dispersion model, a seawater dispersion model, and an air-seawater dispersion model, according to dispersion characteristics of the hazardous and noxious substance (S20).

The sea area state information acquisition unit 114 acquires state information of a sea area that is located around the HNS release region and is differently set according to the dispersion model of the classification set of the HNS, which is determined by the dispersion model determination unit 112, from the weather service center server 200 (S32, S34, S36).

The danger radius prediction unit 116 predicts the danger radius for dispersion of the hazardous and noxious substance using the state information of the sea area, which is acquired by the sea area state information acquisition unit 114 (S42, S44, S46).

More specifically, when the suitable dispersion model for the classification set of the hazardous and noxious substance is determined as being the air dispersion model by the dispersion model determination unit 112, that is, when the hazardous and noxious substance released into the ocean is classified as the air dispersion model, the sea area state information acquisition unit 114 acquires the wind direction and the wind speed of the sea area into which the hazardous and noxious substance is released, from the weather service center server 200 which corresponds to the external server (S32). The danger radius prediction unit 116 calculates the danger radius for dispersion of the hazardous and noxious substance by applying the obtained wind direction and speed to the air dispersion model, and outputs the calculation result through the output unit 124 (S42). Also, information on the calculated air danger radius for dispersion may be transmitted to an external device through the communication unit 120.

When the dispersion model of the classification set of the hazardous and noxious substance is determined as being the sea water dispersion model by the dispersion model determination unit 112, the sea area state information acquisition unit 114 acquires the flow direction and the flow velocity of seawater in the sea area around the HNS release region, from the weather service center server 200. In this case, the sea area state information acquisition unit 114 may optionally acquire at least one of water temperature and salinity of the sea area from the weather service center server 200 (S34). The danger radius prediction unit 116 calculates the danger radius for dispersion of the hazardous and noxious substance by applying the flow direction, flow velocity, water temperature, and salinity of the sea area obtained from the weather service center server 200 to the sea water dispersion model (S44). The calculated in-seawater danger radius for dispersion may be output through the output unit 124 under the control of the control unit 118. Alternatively, the calculated danger radius for dispersion may be transmitted to an external device through the communication unit 120.

The HNS dispersion prediction apparatus according to the embodiment of the present invention may acquire other state information on the sea area in addition to the flow direction, flow velocity, water temperature, and salinity, and may use the acquired information in calculating the in-seawater danger radius for dispersion.

On the other hand, when the dispersion model of the classification set of the released hazardous and noxious substance is determined as being the air-seawater dispersion model by the dispersion model determination unit 112, the sea area state information acquisition unit 114 acquires, from the weather service center server 200, the state information of the sea area required for the air dispersion model, including the wind direction and the wind speed of the sea area around the HNS release region, and the state information of the sea area required for the seawater dispersion model, including the flow direction, flow velocity, water temperature, and salinity of the sea area (S36). The danger radius prediction unit 116 calculates the danger radius for dispersion of the hazardous and noxious substance in the air and in the sea water, using the obtained state information (S46). The calculated airborne danger radius for dispersion and the calculated in-seawater danger radius for dispersion may be output through the output unit 124 under the control of the controller 118. Additionally or alternatively, the airborne and in-seawater calculated danger radius for dispersion may be transmitted to an external device through the communication unit 120.

As described above, the present invention calculates the danger radius for dispersion of the hazardous and noxious substance by applying the state information of the sea area around the HNS release region to a different dispersion model according to the dispersion characteristics of the hazardous and noxious substance. Therefore, the present invention enables a quick and efficient response to marine spills of hazardous and noxious substances.

The method of predicting dispersion of hazardous and noxious substances, according to the present invention, may be implemented in the form of program instructions which can be executed by various computers and may be recorded on a computer-readable recording medium. The computer-readable recording medium may store program instructions, data files, data structures, and the like, singly or in combination thereof. The program instructions recorded on the computer-readable recording medium may be those specifically designed and constructed for the present invention or may be those available to those skilled in computer software.

Examples of computer-readable media include: magnetic media such as hard disks, floppy disks and magnetic tape; optical recording media such as CD-ROMs and DVDs; magnetic-optical media such as floptical disks; and specific hardware devices such as ROMs, RAMs, and flash memories, which are configured to store and execute program instructions.

Examples of program instructions include machine language code such as those produced by a compiler, as well as high-level language code that can be executed by a computer using an interpreter or the like. A hardware device may be configured as one or more software modules to perform the operations of the present invention, and vice versa.

Although the present invention has been described with reference to preferred embodiments, the preferred embodiments are presented to describe the technical spirit of the present invention only for illustrative purposes and those skilled in the art will appreciate that various modifications and changes are possible, without departing from the scope and spirit of the present invention. Therefore, it should be understood that the protection scope of the present invention is defined by the accompanying claims rather than the description which is presented above.

INDUSTRIAL APPLICABILITY

The present invention may be applied to a marine pollution control industry.

The invention claimed is:

1. An apparatus for predicting dispersion of a hazardous and noxious substance (HNS), the apparatus comprising:
   a classification set classifying unit for identifying a state of the HNS resulting from a marine spill accident as one of gas, liquid and solid, determining classification factors based on at least one of a vapor pressure, a water solubility, and a density of the HNS, and then classifying the HNS into a corresponding classification set out of 12 classification sets by using the classification factors;
   a dispersion model determination unit for determining a suitable dispersion model for the classified classification set of the HNS by selecting one dispersion model among an air dispersion model, a sea water dispersion model, and an air-seawater dispersion model, according to a dispersion characteristic of the HNS;
   a sea area state information acquisition unit for acquiring state information of a current sea area that is set according to the determined dispersion model from an external server;
   a danger radius prediction unit for predicting a danger radius for dispersion using the acquired state information of the current sea area; and
   a controller for controlling overall operation for predicting the danger radius for dispersion by controlling the classification set classifier, the dispersion model determination unit, the sea area state information acquisition unit, and the danger radius prediction unit.

2. The apparatus according to claim 1, wherein when the dispersion model of the HNS is determined as being the air dispersion model, the sea area state information acquisition unit acquires wind direction and wind speed of a sea area around an HNS release region, from a water station server that is an external server, and calculates a danger radius for dispersion using the wind direction and the wind speed that are acquired.

3. The apparatus according to claim 1, wherein when the dispersion model is determined as being the seawater dispersion model, the sea area state information acquisition unit acquires state information including flow direction, flow velocity, water temperature, and salinity of a sea area around an HNS release region, from a weather service center server, and calculates the danger radius for dispersion on the basis of the acquired state information including the flow direction, flow speed, water temperature, and salinity.

4. The apparatus according to claim 1, wherein when the dispersion model is determined as being the air-seawater dispersion model, the sea area state information acquisition unit acquires state information including wind direction and wind speed of a sea area around an HNS release region and state information including flow direction, flow velocity, water temperature, and salinity of a sea area around an HNS release region, from a weather service center server corresponding to the external server, and calculates a danger radius for dispersion of the HNS using the acquired state information.

5. A method of predicting dispersion of a hazardous and noxious substance (HNS), the method comprising:
   a first step of identifying a state of the HNS released into a sea area and determining classification factors based on at least one of vapor pressure, water solubility, density of the HNS;
   a second step of classifying the HNS into one corresponding set of 12 classification sets by using the classification factors;
   a third step of determining a suitable dispersion model for the determined classification set by selecting one dispersion model among an air dispersion model, a seawater dispersion model, and an air-seawater dispersion model according to dispersion characteristics of substances of the classification set; and
   a fourth step of acquiring state information of a sea area that is set according to the determined dispersion model and is disposed around an HNS release region, from an external server, and predicting and outputting a danger radius for dispersion by using the acquired state information of the sea area.

6. The method according to claim 5, wherein at the third step, when the dispersion model is determined as being the air dispersion model, wind direction and wind speed of the sea area around the HNS release region, from a weather service center server corresponding to the external server, and a danger radius for dispersion is calculated and output by using the wind direction and speed.

7. The method according to claim 5, wherein at the third step, when the dispersion model is determined as being the seawater dispersion model, flow direction, flow velocity, water temperature, and salinity of the sea area of the HNS release region are obtained from a weather service center server corresponding to the external server, and the danger radius for the dispersion is calculated and output by using the obtained flow direction, flow velocity, water temperature, and salinity.

8. The method according to claim 5, wherein
   at the third step, the dispersion model is determined as being the air-seawater dispersion model, state information of the sea area for the air dispersion model and state information of the sea area for the seawater dispersion model are obtained from a weather service center server, and the danger radius for diffusion is calculated and output by using the obtained state information, and
   the state information required for the air dispersion model includes wind direction and wind speed and the state information required for the seawater dispersion model includes flow direction, flow velocity, water temperature, and salinity.

9. A non-transitory computer-readable recording medium having a program recorded thereon, the program enabling a computer to execute the method according to claim 5.

* * * * *